(12) United States Patent
Marchand et al.

(10) Patent No.: US 8,850,906 B2
(45) Date of Patent: Oct. 7, 2014

(54) FLUID SAMPLING DEVICE

(75) Inventors: Roger L. Marchand, St. Albert (CA); Douglas J. Tschetter, St. Albert (CA)

(73) Assignee: Bay6 Solutions Inc., St. Albert, Alberta (CA)

( * ) Notice: Subject to any disclaimer, the term of this patent is extended or adjusted under 35 U.S.C. 154(b) by 575 days.

(21) Appl. No.: 13/268,023

(22) Filed: Oct. 7, 2011

(65) Prior Publication Data

US 2012/0085183 A1  Apr. 12, 2012

Related U.S. Application Data

(60) Provisional application No. 61/391,001, filed on Oct. 7, 2010, provisional application No. 61/419,165, filed on Dec. 2, 2010.

(51) Int. Cl.
*G01N 1/14*   (2006.01)

(52) U.S. Cl.
CPC ........................................ *G01N 1/14* (2013.01)
USPC ........................................................ 73/864.35

(58) Field of Classification Search
None
See application file for complete search history.

(56) References Cited

U.S. PATENT DOCUMENTS

| | | | | |
|---|---|---|---|---|
| 3,039,309 | A * | 6/1962 | Vesper et al. | 73/863.24 |
| 3,412,613 | A | 11/1968 | Brown et al. | |
| 3,465,595 | A * | 9/1969 | Tansony | 73/864.35 |
| 4,121,907 | A | 10/1978 | Roque | |
| 4,417,232 | A | 11/1983 | Tewfik | |
| 4,548,088 | A | 10/1985 | Hood, Jr. | |
| 4,612,815 | A * | 9/1986 | Green et al. | 73/864.11 |
| 4,628,749 | A | 12/1986 | Rafter, Jr. | |
| 4,713,974 | A * | 12/1987 | Stone | 73/864.23 |
| 4,925,627 | A | 5/1990 | Johnson | |
| 5,070,738 | A * | 12/1991 | Morgan | 73/863.83 |
| 5,341,691 | A * | 8/1994 | Callis et al. | 73/863.83 |
| 5,925,833 | A * | 7/1999 | Peterson | 73/863.72 |
| 6,546,819 | B1 | 4/2003 | Schadt et al. | |
| 7,437,958 | B2 * | 10/2008 | Sharma et al. | 73/863.84 |
| 7,730,796 | B2 * | 6/2010 | Shimada et al. | 73/863.83 |
| 7,921,739 | B2 | 4/2011 | Fjerdingstad et al. | |
| 2010/0206093 | A1 * | 8/2010 | Wright et al. | 73/863.11 |

FOREIGN PATENT DOCUMENTS

WO  WO 97/29353  8/1997

OTHER PUBLICATIONS

OELCHEK Oil Sampling Pump. Available at http://www.oelcheck.de/fileadmin/oelcheck/pdf_eng/OELCHEK-Sample-Pump.pdf since at least as early as Mar. 2011.

(Continued)

*Primary Examiner* — Robert R Raevis
(74) *Attorney, Agent, or Firm* — Davis & Bujold, PLLC; Michael J. Bujold

(57) ABSTRACT

A device for sampling fluids that has an outer conduit having a first end connected to a non-pressurized fluid reservoir and a second end adjacent to the testing location that is remote from the fluid reservoir. An inner fluid conduit is positioned within the outer conduit, the inner fluid conduit having a first end extending into the fluid reservoir and the second end adjacent to the testing location, the second end having a connector. A pressure source selectively connects to the connector and selectively applies a vacuum to the second end of the inner fluid conduit to draw fluid from the through the inner fluid conduit and applying pressure to purge the inner fluid conduit of fluid.

25 Claims, 5 Drawing Sheets

(56) References Cited

OTHER PUBLICATIONS

Oil Analysis. Available at http://www.wearcheck.com/info/manage_take_samples.asp since at least as early as Sep. 2011.

Sample Ports. Herguth Laboratories, Inc. Available at http://www.herguth.com/technical/Special_Sampling_Ports.pdf since at least as early as Apr. 2006.

* cited by examiner

FLUID SAMPLING DEVICE

FIELD

This relates to a fluid sampling device for obtaining a sample from a remote location.

BACKGROUND

It is often necessary to draw fluids from a fluid reservoir for testing purposes. Hand pumps and electric pumps are often used to draw fluid into a sample container.

SUMMARY

There is provided a device for sampling fluids, comprising a fluid conduit having an inlet in communication with fluids to be sampled, and an outlet connected to a sample container. A pressure source selectively applies a vacuum to draw fluid through the fluid conduit into the sample container and applies pressure to purge the fluid conduit of fluid.

According to another aspect, there is provided a device for sampling fluids, comprising an outer conduit having a first end connected to a non-pressurized fluid reservoir and a second end adjacent to the testing location that is remote from the fluid reservoir, and an inner fluid conduit positioned within the outer conduit, the inner fluid conduit having a first end extending into the fluid reservoir and the second end adjacent to the testing location, the second end having a connector. A pressure source selectively connects to the connector and selectively applies a vacuum to the second end of the inner fluid conduit to draw fluid through the inner fluid conduit and applying pressure to purge the inner fluid conduit of fluid.

According to another aspect, the fluid reservoir may be a hydraulic reservoir for a vehicle, and the testing location may be a vehicle access opening.

According to another aspect, the fluid reservoir comprises a removable cap, the first end of the outer conduit being connected to the removable cap.

According to another aspect, the inner fluid conduit may be removable from the outer conduit, and the first end of the inner fluid conduit may comprise a fluid level indicator. The fluid level indicator may comprise a concave surface.

According to another aspect, the pressure source may draw fluid into a sample container, and the pressure source may connect to the connector of the inner fluid conduit via the sample container.

According to another aspect, there is provided, in combination, inner and outer conduits, a pressure source, a sample container, and a connector. The inner fluid conduit are positioned within the outer conduit, the outer conduit being connected between a fluid reservoir and an testing location spaced from the fluid reservoir, the inner fluid conduit having a first end that extends into the fluid reservoir and a second end adjacent to the access point. The pressure source selectively applies a vacuum to the second end of the inner fluid conduit to draw fluid through the inner fluid conduit into the sample container and applying pressure to purge the inner fluid conduit of fluid. The sample container collects fluid drawn through the inner conduit. A connector selectively connects the pressure source, the second end of the inner conduit, and the sample container.

According to another aspect, the fluid reservoir may be a hydraulic reservoir for a vehicle, and the testing location may be a vehicle access opening.

According to another aspect, the fluid reservoir comprises a removable cap, the first end of the outer conduit being connected to the removable cap.

According to another aspect, the inner fluid conduit may be removable from the outer conduit, and the first end of the inner fluid conduit may comprise a fluid level indicator. The fluid level indicator may comprise a concave surface.

According to another aspect, the pressure source may draw fluid into a sample container, and the pressure source may connect to the connector of the inner fluid conduit via the sample container.

According to another aspect, the connector may comprise a lid of the sample container, the lid comprising a first connector for connecting to the inner fluid conduit and a second connector for connecting to the pressure source. The pressure source may connect to the connector of the inner fluid conduit via the sample container.

BRIEF DESCRIPTION OF THE DRAWINGS

These and other features will become more apparent from the following description in which reference is made to the appended drawings, the drawings are for the purpose of illustration only and are not intended to be in any way limiting, wherein.

DETAILED DESCRIPTION

Figure 1:
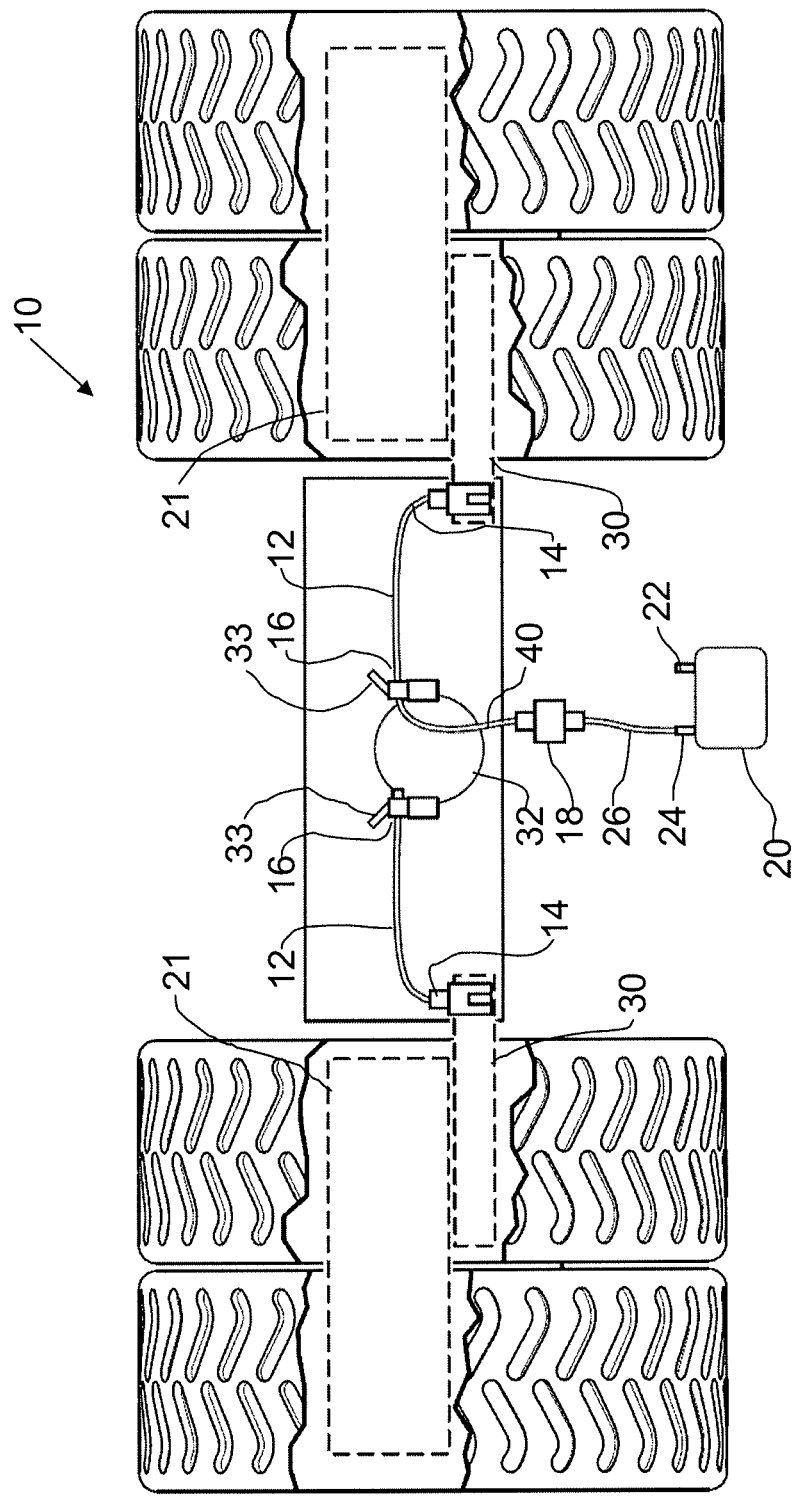
FIG. 1 is a schematic view of a device for sampling fluid.

A device for sampling fluid, generally identified by reference numeral 10, will now be described with reference to FIG. 1 through 9.

Figure 2:
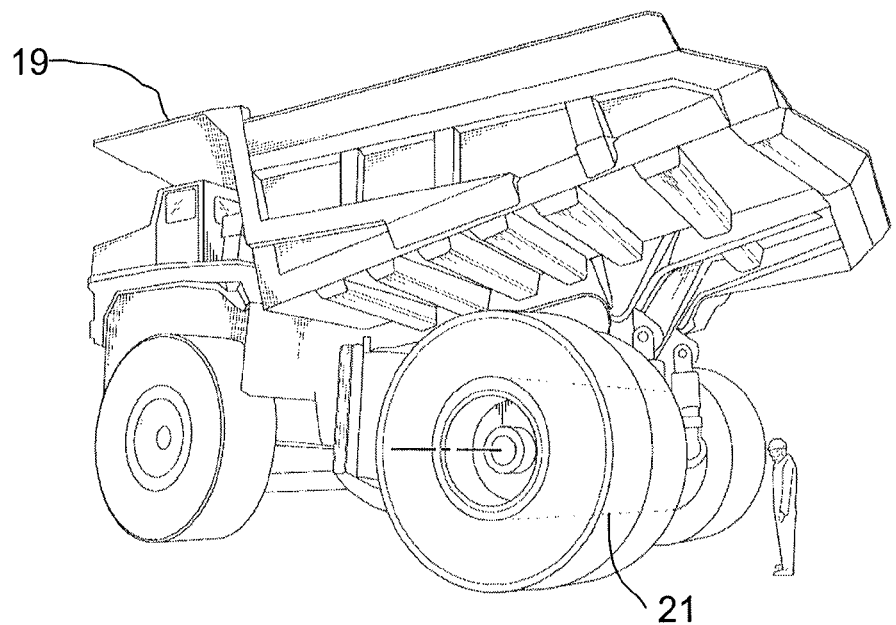
FIG. 2 is a perspective view of a mining truck.
Figure 3:
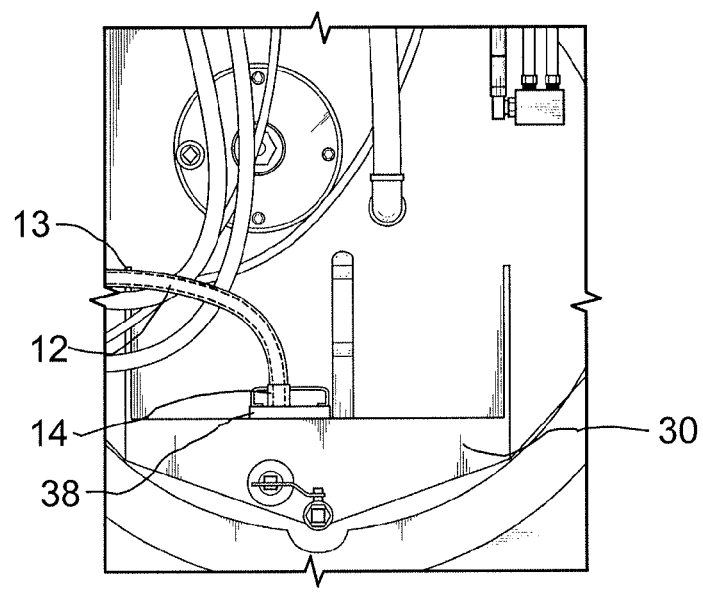
FIG. 3 is a detailed side elevation view of a fluid reservoir.

Structure and Relationship of Parts:

Referring to FIG. 1, device for sampling fluids 10 includes a fluid conduit 12 having an inlet 14 in communication with fluids to be sampled, and an outlet 16 connected to a sample container 18. Referring to FIG. 3, fluid conduit 12 is preferably an inner fluid conduit (shown in dotted lines), and is installed within an outer conduit 13. Outer conduit 13 is used to protect inner fluid conduit 12, and in a preferred embodiment, fluid conduit is removable from outer conduit 13. As outer conduit 13 preferably acts primarily as a guide and protective sheath, it may not be made from impermeable material. Preferably, it will be made from a material that resists damage. Fluid conduit 12 is preferably a flexible hose that can withstand the vacuum pressures necessary to draw fluid into sample container 18, and the pressures necessary to purge the fluid after the sample has been taken. Fluid conduit 12 must be selected to provide a balance between friction between the liquid being sampled and fluid conduit 12, and the viscosity of the fluid being sampled. In the example discussed below where hydraulic fluid from an reservoir in mining truck 19 as shown in FIG. 2, with an electric drive 21 as shown in FIG. 1, adequate results have been achieved using 5/16" hose size.

Figure 8:
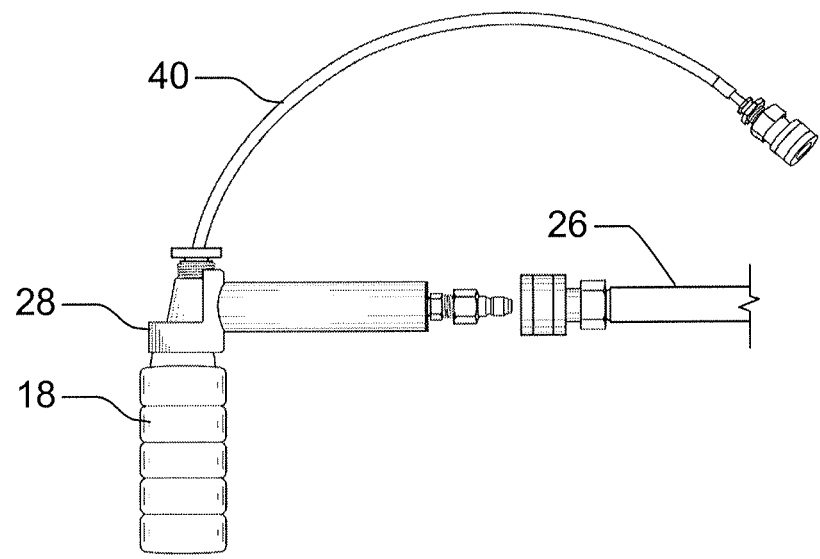
FIG. 8 is a side elevation view of a sample container.
Figure 9:
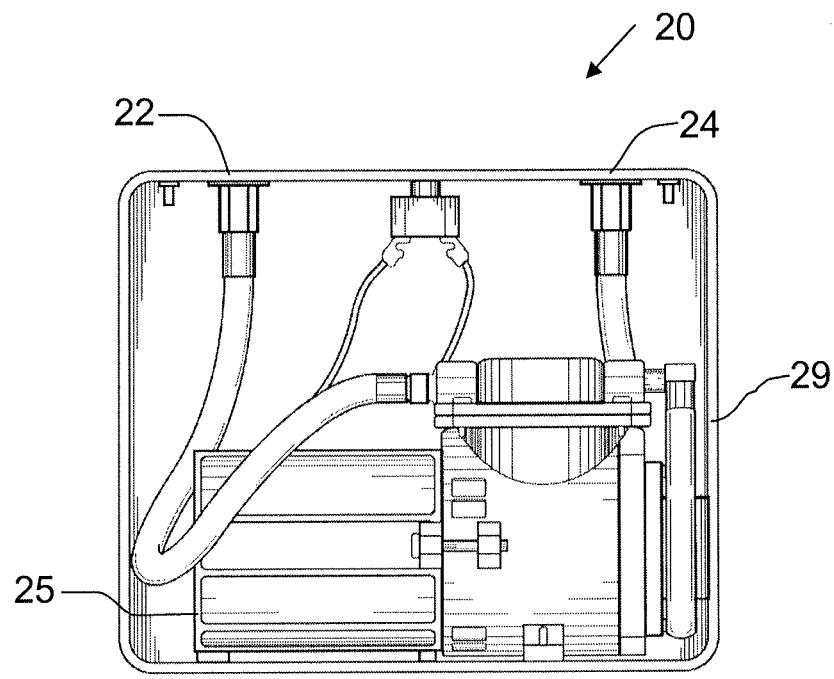
FIG. 9 is a side elevation view of a pressure source.

Referring to FIG. 1, the pressure and vacuum are applied to fluid conduit 12 by a pressure source 20 that has a pressure mode and a vacuum mode. Referring to FIG. 9, pressure source 20 preferably has a pressure port 22 and a vacuum port 24 that are that are connected to an electric compressor 25, where the mode of pressure source 20 is changed by making the appropriate connection. Referring again to FIG. 1, pressure source 20 is used to apply a vacuum to draw fluid through fluid conduit 12 into sample container 18 and then to apply pressure to purge the fluid conduit of fluid. As depicted, sample container 18 is connected to pressure source 20 by another hose 26. Referring to FIG. 8, the connection between fluid conduit 12, pressure source 20 and an example of a sample container 18 are preferably made though the lid 28 of sample container 18. As shown in FIG. 1, fluid conduit 12 is connected to lid 28 via hose 40, and pressure source 20 is connected to lid 28 via hose 26. Pressure source 20 can then apply positive or negative pressure to the sample container 18 to draw fluids through or purge fluid from fluid conduit 12 until it is disconnected from lid 28. It will be understood that pressure source 20 may be connected to fluid conduit 12 in different ways in order to collect a fluid sample, depending on the design of pressure source 20 and sample container 18. However, the design described permits the device to be used with commonly available equipment and products.

In one embodiment, referring to FIG. 9 pressure source 20 is a 12 V vacuum/compressor 25 that can be powered by a standard power outlet in a vehicle or by a battery pack. Pressure source 20 is preferably portable and is contained within a carrying case 29. Pressure source 20 may also have a transformer that allows it to be powered from a standard 110 V socket, or other common power supply. There may be a filter included to protect the components (not shown). In other embodiments, an air pressure regulator and a vacuum generator may be used to accommodate a pressurized air source.

Figure 4:
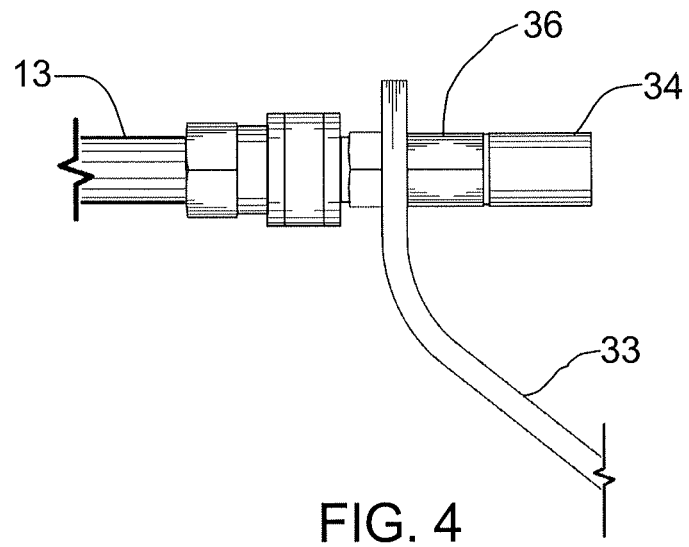
FIG. 4 is a side elevation view of an attachment for attaching the fluid conduit adjacent to an access point.
Figure 5:
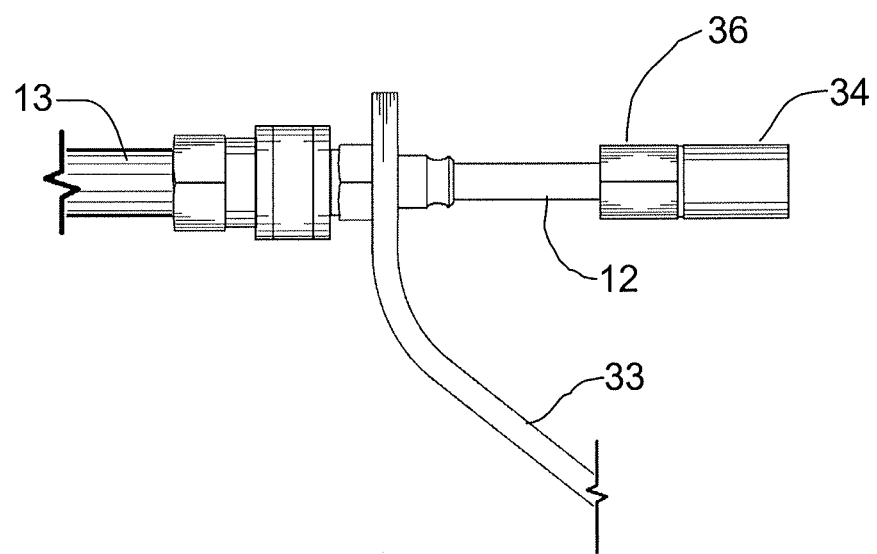
FIG. 5 is a side elevation view of the attachment of FIG. 4 with an inner conduit being withdrawn from an outer conduit.

In a preferred embodiment, referring to FIG. 1, device 10 is used to draw fluids from an unpressurized fluid reservoir 30 that is remote from an access point 32. For example, in electric drive mining trucks 19, oil is often contained in reservoir 30 that is spaced from an access point 32, such as a manway. This requires personnel to enter a confined compartment to reach the fluid reservoir 30 when it is necessary to obtain a fluid sample. Referring to FIG. 1, fluid conduit 12 is installed with inlet 14 in constant communication with fluid reservoir 30, while outlet 16 is mounted adjacent to access point 32 using a bracket 33, as shown in FIG. 4. Bracket 33 is shaped such that outlet 16 is held recessed from access point 32 to prevent any interference with opening and closing access point 32. Outlet 16 is preferably designed with a quick-connect nipple 34, so that sample container 18 may be easily connected and disconnected. Referring to FIG. 5, in order to remove fluid conduit 12 from outer conduit 13, fluid conduit 12 preferably has a connector 36 that connects to bracket 33.

Figure 6:
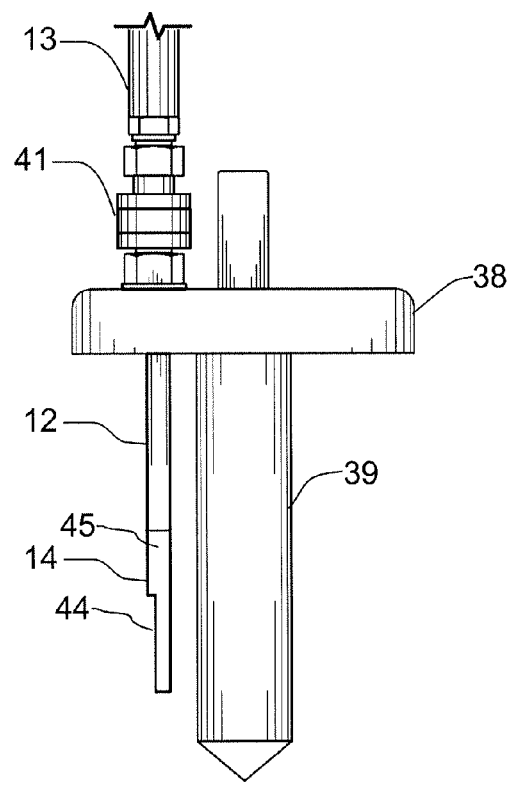
FIG. 6 is a side elevation view of a fluid conduit attached to a cap for a fluid reservoir.
Figure 7:
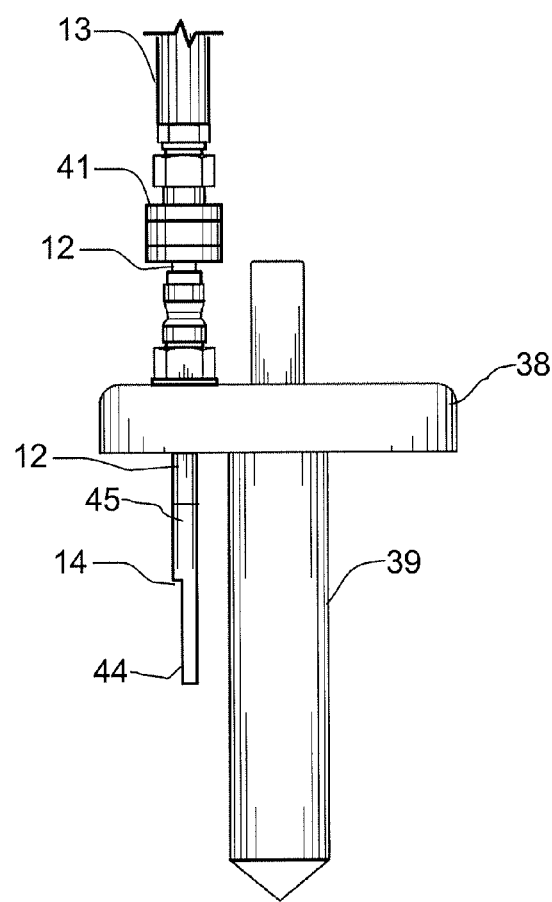
FIG. 7 is a side elevation view of the fluid reservoir of FIG. 6 with the fluid conduit being detached from the cap.

Inlet 14 may be mounted to fluid reservoir 30 by various means. In the example shown in FIG. 3, inlet 14 is mounted to a cap 38 of the fluid reservoir 30. By having fluid conduit 12 pass through cap 38, cap 38 does not need to be removed, which reduces the risk of contaminating fluid reservoir 30 when compared with the traditional method of removing cap 38 to insert a fluid sampler. As depicted in FIGS. 6 and 7, cap 38 is also used to hold a magnetic filter element 39. Many cap designs that are common on non-pressurized tanks are suitable and may be used. As shown, outer conduit 13 is attached by a swivel connection 41. Other types of connections may be used. This allows cap 38 to be easily removed or installed for service. Inner conduit 12 is preferably not secured directly to cap 38 to allow it to be removed by releasing connection 36. Alternatively, if inner conduit 12 is not removable, a quill tube (not shown) may be attached to cap 38 that extends downward into oil reservoir 30 to act as the inlet 14 end of hose 12. As depicted in FIGS. 6 and 7, outer conduit 13 preferably attaches to cap 38, and inner fluid conduit 12 may pass through cap 38 to access fluid directly. Preferably, the connections between inner conduit 12, outer conduit 13 and cap 38 are swivel connections to prevent twisting of the conduits during installation.

As mentioned above, fluid conduit 12 is preferably removable, such that it can also act as a dip stick. In other embodiments, it may be desirable to provide a fluid level indicator, or "dip stick" that can be inserted through the outer conduit 13 or inner conduit 12 to check the fluid level in the fluid reservoir 30. Alternatively, there may be a hole in the portion of fluid conduit 12 that is intended to be submerged in oil to act as a vacuum break. In this example, if the fluid level is below the minimum threshold, fluid will not be extracted through conduit 12.

Referring to FIG. 6, inlet 14 of fluid conduit 12 has a minimum fluid level indicator portion 44, which consists of a cutaway portion of the tube. This forms a vacuum break that prevents a sample from being drawn if the fluid level is below a minimum threshold. In addition, the bottom of fluid conduit 12 may be used as a fluid level indicator, i.e. a dipstick. This may be done by texturing the outer surface at the bottom 45 of fluid conduit 12, such as by sanding, so that any oil will adhere to the surface and allow an operator to check the level. This embodiment allows the same tubing 12 to be used to remove a fluid sample by technicians, and as a fluid level check by operators. Outer conduit 12 may also be connected to the reservoir cap by a swivel connection to prevent twisting during installation. Referring to FIGS. 4 and 5, fluid conduit 12 preferably has a quick connect nipple coupler 34 to connect to pressure source 20 in order to purge fluid back into reservoir 30. Outer conduit conduit 13 may terminate at mounting bracket 33 as shown, or it may be mounted in other ways that will be apparent to those skilled in the art.

Operation:

Referring to FIG. 1, fluid conduit 12 is installed with inlet 14 in communication with fluid reservoir 30 and outlet 16 mounted adjacent to an access point 32, such as a manway in the housing that houses fluid reservoir 30. When it is necessary to draw a sample, manway 32 is opened, and sample container 18 is attached to fluid conduit 12. As shown, sample container 18 has an additional hose 40 to connect to fluid conduit 12. Vacuum port 24 of pressure source 20 is then connected via hose 26 to sample container 18 to apply vacuum pressure to sample container 18 to draw a sample from fluid reservoir 30 into sample container 18 through inner conduit 12 via hose 40. Generally, two sample containers 18 are filled, with the first being drawn to flush the line and is discarded. Once the necessary samples are obtained, fluid conduit 12 is connected to pressure port 22, either directly or through sample container 18, to blow down any remaining fluid in fluid conduit 12. As there will generally be two reservoirs 30 for each axle tube, the process is repeated for the other reservoir 30. There will preferably be a fluid conduit 12 installed for each reservoir 30, such that pressure source 20 is reconnected by a new sample container 18 to another fluid conduit 12.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

The following claims are to be understood to include what is specifically illustrated and described above, what is conceptually equivalent, and what can be obviously substituted. Those skilled in the art will appreciate that various adaptations and modifications of the described embodiments can be configured without departing from the scope of the claims. The illustrated embodiments have been set forth only as examples and should not be taken as limiting the invention. It is to be understood that, within the scope of the following claims, the invention may be practiced other than as specifically illustrated and described.

What is claimed is:

1. A device for sampling fluids from a non-pressurized fluid reservoir, comprising:
   an outer conduit having a connector at a first end that connects to the fluid reservoir and a second end adjacent to a sampling location that is remote from the fluid reservoir;
   an inner fluid conduit positioned within the outer conduit, the inner fluid conduit having a first end extending into the fluid reservoir and the second end adjacent to the sampling location, the second end having a connector; and
   a pressure source that selectively connects to the connector and selectively applies a vacuum to the second end of the inner fluid conduit to draw fluid through the inner fluid conduit and selectively applies pressure to purge the inner fluid conduit of fluid.

2. The device of claim 1, wherein the fluid reservoir is a hydraulic reservoir for a vehicle, and the sampling location is a vehicle access opening.

3. The device of claim 1, wherein the fluid reservoir comprises a removable cap, the first end of the outer conduit being connected to the removable cap.

4. The device of claim 1, wherein the inner fluid conduit is movably positioned within the outer conduit.

5. The device of claim 4, wherein the first end of the inner fluid conduit comprises a fluid level indicator.

6. The device of claim 5, wherein the fluid level indicator comprises a textured surface.

7. The device of claim 5, wherein the fluid level indicator comprises a vacuum break.

8. The device of claim 1, wherein the pressure source draws fluid into a sample container.

9. The device of claim 8, wherein the pressure source connects to the connector of the inner fluid conduit via the sample container.

10. The device of claim 1, wherein the outer conduit and the inner fluid conduit are made from flexible materials.

11. In combination:
    a fluid reservoir of a vehicle;
    an inner conduit and an outer conduit, the inner conduit being positioned within the outer conduit, the outer conduit being connected between the fluid reservoir and a sampling location spaced from the fluid reservoir, the second conduit having a first end that extends into the fluid reservoir and a second end adjacent to the sampling location;
    a pressure source for selectively applying a vacuum to the second end of the inner conduit to draw fluid through the inner conduit into a sample container and applying pressure to purge the inner conduit of fluid;
    the sample container collecting fluid drawn through the inner conduit; and
    a connector for selectively connecting the pressure source, the second end of the inner conduit, and the sample container.

12. The combination of claim 11, wherein the sampling location is a vehicle access opening.

13. The combination of claim 11, wherein the fluid reservoir comprises a removable cap, the first end of the outer conduit being connected to the removable cap.

14. The combination of claim 11, wherein the inner fluid conduit is movably positioned within the outer conduit.

15. The combination of claim 14, wherein the first end of the inner fluid conduit comprises a fluid level indicator.

16. The combination of claim 15, wherein the fluid level indicator comprises a textured surface.

17. The combination of claim 15, wherein the fluid level indicator comprises a vacuum break.

18. The combination of claim 11, wherein the connector comprises a lid of the sample container, the lid comprising a first connector for connecting to the inner fluid conduit and a second connector for connecting to the pressure source.

19. The device of claim 18, wherein the pressure source connects to the connector of the inner fluid conduit via the sample container.

20. The combination of claim 11, wherein the outer conduit is connected by a connector to the fluid reservoir.

21. The combination of claim 11, the outer conduit and the inner conduit are made from flexible materials.

22. A method of sampling fluids in a non-pressurized fluid reservoir, comprising the steps of:
    connecting a connector at a first end of an outer conduit to the fluid reservoir and attaching a second end adjacent to a sampling location that is remote from the fluid reservoir;
    positioning an inner fluid conduit within the outer conduit, the inner fluid conduit having a first end extending into the fluid reservoir and the second end adjacent to the sampling location, the second end having a connector;
    collecting a sample by applying a vacuum to the second end of the inner fluid conduit to draw fluid through the inner fluid conduit; and
    applying pressure to the second end of the inner fluid conduit to purge the inner fluid conduit of fluid.

23. The method of claim 22, further comprising the step of checking a fluid level in the fluid reservoir by removing the inner fluid conduit from the outer conduit, the first end comprising a fluid level indicator.

24. The method of claim 22, wherein the connector is connected to the fluid reservoir of a vehicle.

25. The method of claim 22, wherein the outer conduit and the inner fluid conduit are made from flexible materials.

* * * * *